US009839220B2

(12) United States Patent
Evans et al.

(10) Patent No.: US 9,839,220 B2
(45) Date of Patent: Dec. 12, 2017

(54) ANTIMICROBIAL ABRASIVE CREAM TYPE CLEANING COMPOSITIONS FOR INANIMATE HARD SURFACES

(71) Applicant: Reckitt Benckiser (Brands) Limited, Slough, Berkshire (GB)

(72) Inventors: Mark Evans, Hull (GB); Jason Geno, Westwood, NJ (US); Michael Maledi, Dubai (AE)

(73) Assignee: RECKITT BENCKISER (BRANDS) LIMITED, Slough, Berkshire (GB)

( * ) Notice: Subject to any disclaimer, the term of this patent is extended or adjusted under 35 U.S.C. 154(b) by 0 days.

(21) Appl. No.: 14/760,325

(22) PCT Filed: Dec. 5, 2013

(86) PCT No.: PCT/GB2013/053209
§ 371 (c)(1),
(2) Date: Jul. 10, 2015

(87) PCT Pub. No.: WO2014/108664
PCT Pub. Date: Jul. 17, 2014

(65) Prior Publication Data
US 2015/0351405 A1    Dec. 10, 2015

(30) Foreign Application Priority Data
Jan. 14, 2013   (GB) .................................. 1300584.8

(51) Int. Cl.
*A01N 47/30*   (2006.01)
*C11D 3/12*    (2006.01)
*A01N 31/08*   (2006.01)
*A01N 25/22*   (2006.01)
*C11D 3/24*    (2006.01)
*C11D 1/12*    (2006.01)
*C11D 1/66*    (2006.01)
*C11D 3/22*    (2006.01)
*C11D 1/83*    (2006.01)
*C11D 3/48*    (2006.01)

(52) U.S. Cl.
CPC ............ *A01N 47/30* (2013.01); *A01N 25/22* (2013.01); *A01N 31/08* (2013.01); *C11D 1/12* (2013.01); *C11D 1/66* (2013.01); *C11D 1/83* (2013.01); *C11D 3/12* (2013.01); *C11D 3/1233* (2013.01); *C11D 3/222* (2013.01); *C11D 3/24* (2013.01); *C11D 3/48* (2013.01)

(58) Field of Classification Search
None
See application file for complete search history.

(56) References Cited

U.S. PATENT DOCUMENTS

| 6,066,606 A * | 5/2000 | Lu ............................. C11D 1/94 423/424 |
| 6,342,473 B1 * | 1/2002 | Kott ........................ C11D 1/22 510/357 |
| 6,617,293 B2 * | 9/2003 | Chen ....................... C11D 1/83 510/125 |

FOREIGN PATENT DOCUMENTS

| EP | 0126545 A1 | 4/1984 |
| GB | 2305434 A | 4/1997 |
| GB | 2393908 A | 4/2004 |
| WO | 9830672 A1 | 7/1998 |
| WO | 9849261 A1 | 11/1998 |
| WO | 03022240 A2 | 3/2003 |
| WO | 2006097238 A1 | 9/2006 |

OTHER PUBLICATIONS

20 Mule Team® Borax (on-line published since Jun. 7, 2009 as evidenced by wayback machine website which is retrieved from on-line website: http://web.archive.org/web/20090706063534/ http://www.20muleteamlaundry.com/about, last visit Feb. 23, 2017]).*
CCI, "Safety Data Sheet of Monoethanolamine", 2014, pp. 1-6.*
GB Search Report for GB 1300584.8 dated May 13, 2013.
International Search Report and the Written Opinion of the International Searching Authority for PCT/GB2013/053209 dated Jun. 26, 2014.

* cited by examiner

*Primary Examiner* — Ernst V Arnold
*Assistant Examiner* — Kyung Sook Chang
(74) *Attorney, Agent, or Firm* — Norris McLaughlin & Marcus PA

(57) ABSTRACT

The present invention provides aqueous alkaline, storage stable, abrasive containing hard surface treatment compositions which provide good cleaning to a treated hard surface, and concurrently a useful sanitizing or disinfecting benefit to such treated surfaces, wherein the compositions comprise: 0.01-15% wt. of at least one anionic surfactant and at least one nonionic surfactant, and preferably wherein the amount of the at least one anionic surfactant is in excess of the amount of the at least one nonionic surfactant; 0.1-50% wt. of one or more inorganic abrasive particulate materials which are based on inorganic carbonate compounds; a thickener; at least one non-cationic germicide constituent, which preferably are one or more compounds selected from the group consisting of: parachlorometaxylenol, and halogenated carbanilides (e.g., 3,4,4'-trichlorocarbanilide (also referred to as Triclocarban® or TCC), 3-trifluoromethyl-4, 4-dichlorocarbanilide, and 3,3,4-trichlorocarbanilide; and, water, wherein the compositions preferably exhibit a pH in the range of 7-10.5, a viscosity of 1000-3000 cPs, when measured at 25° C., and wherein the compositions provide an antimicrobial benefit to treated hard surfaces.

14 Claims, No Drawings

ANTIMICROBIAL ABRASIVE CREAM TYPE CLEANING COMPOSITIONS FOR INANIMATE HARD SURFACES

This is an application filed under 35 USC 371 of PCT/GB2013/053209, and claims priority to GB Patent Application 1300584.8 filed 14 Jan. 2013. The entirety of these foregoing documents is herein incorporated by reference.

The present invention relates to cream type cleaning compositions which concurrently provide cleaning and an antimicrobial benefit to treated inanimate hard surfaces. The cream type cleaning compositions comprise abrasive particles, which are stably suspended over long periods of time in the cream type cleaning compositions.

While compositions are known to the art which provide a cleaning and optionally a disinfecting benefit to hard surfaces and particularly to inanimate surfaces of kitchens and lavatories, such are frequently based on acidic compositions which provide a good antimicrobial benefit due to the low pH of the compositions. Other known art compositions which provide good antimicrobial benefits to hard surfaces are those which are based on germicidally effective cationic compounds, e.g., quaternary ammonium halides which provide a good antimicrobial benefit but as these germicidally effective cationic compounds are incompatible with anionic compounds due to undesirable reactions between such anionic and cationic compounds, such known art compositions which include germicidally effective cationic compounds frequently provide poorer cleaning benefits to treated hard surfaces. Also, such germicidally effective cationic compounds are frequently incompatible with many thickeners. Thus, there is nonetheless a real and continuing need in the art to provide viscous hard surface treatment compositions which provide an improved cleaning, and desirably also a simultaneous sanitizing or disinfecting benefit to treated hard surfaces. Particularly there is a real need in the art for viscous, abrasive-containing hard surface cleaning compositions useful in the treatment of in providing both a cleaning and antimicrobial benefit to hard surfaces which feature good storage stability, and which are readily applied from a container, especially a squeeze bottle onto a hard surface.

Accordingly, it is among the aspects of the invention to provide improved hard surface treatment compositions which provide the benefits of good cleaning to a treated hard surface, and concurrently a useful sanitizing or disinfecting benefit to such treated surfaces.

A yet further aspect of the invention is a storage stable, abrasive containing hard surface treatment composition which features the benefits described above.

A yet further aspect of the invention is a method for the manufacture of the improved hard surface treatment compositions which feature the benefits described above.

These and further aspects of the present inventive composition will become more evident from a consideration of the following.

In a first aspect the present invention provides an aqueous alkaline, storage stable, abrasive containing hard surface treatment composition which provides good cleaning to a treated hard surface, and concurrently a useful sanitizing or disinfecting benefit to such treated surfaces, wherein the composition comprises:

about 0.01-15% wt. of at least one anionic surfactant and at least one nonionic surfactant, and preferably wherein the amount of the at least one anionic surfactant is preferably in excess of the amount of the at least one nonionic surfactant;

about 0.1-50% wt. of one or more inorganic abrasive particulate materials which are based on inorganic carbonate compounds;

a gum based thickener, preferably wherein the gum based thickener is xanthan gum;

at least one non-cationic germicide constituent, which preferably are one or more compounds selected from the group consisting of: parachlorometaxylenol, and halogenated carbanilides (e.g., 3,4,4'-trichlorocarbanilide (also referred to as Triclocarban® or TCC), 3-trifluoromethyl-4,4-dichlorocarbanilide, and 3,3,4-trichlorocarbanilide;

at least about 50% wt. of water; and, optionally but preferably, a pH adjusting agent and/or a pH buffer;

wherein the composition preferably exhibits a pH in the range of about 7-10.5, a viscosity of at least about 1000 cPs, preferably a viscosity of from about 1200 cps-3000 cPs when measured at 25° C., and wherein the composition provides an antimicrobial benefit to treated hard surfaces.

In a second aspect the present invention provides an aqueous alkaline, storage stable, abrasive containing hard surface treatment composition which provides good cleaning to a treated hard surface, and concurrently a useful sanitizing or disinfecting benefit to such treated surfaces, wherein the composition comprises:

about 0.01-15% wt. of at least one anionic surfactant and at least one nonionic surfactant, and preferably wherein the amount of the at least one anionic surfactant is in excess of the amount of the at least one nonionic surfactant;

about 0.1-50% wt. of one or more inorganic abrasive particulate materials which are based on inorganic carbonate compounds;

a gum based thickener, preferably wherein the gum based thickener is xanthan gum concurrently with a clay based thickener;

at least one non-cationic germicide constituent, which preferably are one or more compounds selected from the group consisting of: parachlorometaxylenol, and halogenated carbanilides (e.g., 3,4,4'-trichlorocarbanilide (also referred to as Triclocarban® or TCC), 3-trifluoromethyl-4,4-dichlorocarbanilide, and 3,3,4-trichlorocarbanilide;

at least about 50% wt. of water; and, optionally but preferably, a pH adjusting agent and/or a pH buffer;

wherein the composition preferably exhibits a pH in the range of about 7-10.5, a viscosity of at least about 1000 cPs, preferably a viscosity of from about 1200 cps-3000 cPs when measured at 25° C., and wherein the composition provides an antimicrobial benefit to treated hard surfaces.

In a third aspect the present invention provides an aqueous alkaline, storage stable, abrasive containing hard surface treatment composition which provides good cleaning to a treated hard surface, and concurrently a useful sanitizing or disinfecting benefit to such treated surfaces, wherein the composition comprises:

about 0.01-15% wt. of at least one anionic surfactant and at least one nonionic surfactant, and preferably wherein the amount of the at least one anionic surfactant is in excess of the amount of the at least one nonionic surfactant;

about 0.1-50% wt. of one or more inorganic abrasive particulate materials which are based on inorganic carbonate compounds;

an acrylate based thickener;

at least one non-cationic germicide constituent, which preferably are one or more compounds selected from the group consisting of: parachlorometaxylenol, and halogenated carbanilides (e.g., 3,4,4'-trichlorocarbanilide (also referred to as Triclocarban® or TCC), 3-trifluoromethyl-4, 4-dichlorocarbanilide, and 3,3,4-trichlorocarbanilide;

at least about 50% wt. of water; and, optionally but preferably, a pH adjusting agent and/or a pH buffer;

wherein the composition preferably exhibits a pH in the range of about 7-10.5, a viscosity of at least about 1000 cPs, preferably a viscosity of from about 1200 cps-3000 cPs when measured at 25° C., and wherein the composition provides an antimicrobial benefit to treated hard surfaces.

According to a fourth embodiment of the invention there is provided an aqueous alkaline, storage stable, abrasive containing hard surface treatment composition according to any of the first, second and third aspects of the invention, wherein there is present as a further essential constituent there is also present 0.001-10% wt. of at least one organic solvent.

In a further aspect the present invention provides a method or production for the manufacture of the aqueous, storage stable, abrasive containing hard surface treatment composition described herein.

In a further aspect the present invention provides as a vendible product a dispensing container which includes the aqueous, storage stable, abrasive containing hard surface treatment composition described herein.

In a further aspect, the present invention provides a method for treatment of hard surfaces in order to provide a cleaning and/or antimicrobial benefit thereto utilizing the aqueous, storage stable, abrasive containing hard surface treatment composition described herein.

In all aspect of the invention the inventive compositions necessarily include at least one nonionic surfactant and at least one nonionic surfactant, and preferably the amount of the at least one anionic surfactant is in excess of the amount of the at least one nonionic surfactant. Whereas the anionic surfactant generally provides a primary cleaning benefit in the treatment of hard surfaces, the inclusion of the nonionic surfactant constituent primarily provides a solubilizing benefit for the poorly soluble constituents, e.g., the a non-cationic germicide constituent, and when present, a fragrance constituent, which are present in the compositions of the invention.

Non-limiting examples of useful anionic surfactants include alkali metal salts, ammonium salts, amine salts, or aminoalcohol salts of one or more of the following compounds (linear and secondary): alcohol sulfates and sulfonates, alcohol phosphates and phosphonates, alkyl sulfates, alkyl ether sulfates, sulfate esters of an alkylphenoxy polyoxyethylene ethanol, alkyl monoglyceride sulfates, alkyl sulfonates, olefin sulfonates, paraffin sulfonates, beta-alkoxy alkane sulfonates, alkylamidoether sulfates, alkylaryl polyether sulfates, monoglyceride sulfates, alkyl ether sulfonates, ethoxylated alkyl sulfonates, alkylaryl sulfonates, alkyl benzene sulfonates, alkylamide sulfonates, alkyl monoglyceride sulfonates, alkyl carboxylates, alkyl sulfoacetates, alkyl ether carboxylates, alkyl alkoxy carboxylates having 1 to 5 moles of ethylene oxide, alkyl sulfosuccinates, alkyl ether sulfosuccinates, alkylamide sulfosuccinates, alkyl sulfosuccinamates, octoxynol or nonoxynol phosphates, alkyl phosphates, alkyl ether phosphates, taurates, N-acyl taurates, fatty taurides, fatty acid amide polyoxyethylene sulfates, isethionates, acyl isethionates, and sarcosinates, acyl sarcosinates, or mixtures thereof. Generally, the alkyl or acyl radical in these various compounds comprise a carbon chain containing 12 to 20 carbon atoms.

Preferred anionic surfactants include alkyl sulfates which may be represented by the following general formula:

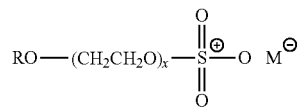

wherein R is an straight chain or branched alkyl chain having from about 8 to about 18 carbon atoms, saturated or unsaturated, and the longest linear portion of the alkyl chain is 15 carbon atoms or less on the average, M is a cation which makes the compound water soluble especially an alkali metal such as sodium, or is ammonium or substituted ammonium cation, and x is from 0 to about 4. Of these, most preferred are the non-ethoxylated $C_{12}$-$C_{15}$ primary and secondary alkyl sulfates, and especially sodium lauryl sulfate.

Further preferred anionic include alkyl sulfonate anionic surfactants which may be represented according to the following general formula:

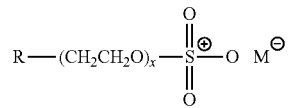

wherein R is an straight chain or branched alkyl chain having from about 8 to about 18 carbon atoms, saturated or unsaturated, and the longest linear portion of the alkyl chain is 15 carbon atoms or less on the average, M is a cation which makes the compound water soluble especially an alkali metal such as sodium, or is ammonium or substituted ammonium cation, and x is from 0 to about 4. Of these, preferred are the $C_{12}$-$C_{15}$ primary and secondary alkyl sulfates.

Also considered to be anionic surfactants in this invention are fatty acid based soaps. Such include anionic materials (i.e. alkali metal salts, e.g., sodium or potassium salts) of fatty acids, typically having from about 8 to about 24 carbon atoms, preferably from about 10 to about 20 carbon atoms. Further suitable soaps include alkali metal, ammonium and alkanolammonium salts of aliphatic alkane or alkene mono-carboxylic acids having about 8 to about 18 carbon atoms. Sodium, potassium, ammonium, mono-, di-, and triethanolammonium cations or combinations thereof, are preferred. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps may be prepared by either direct saponification of fats and oils or by neutralization of free fatty acids. Particularly useful are the sodium, potassium, ammonium and alkanolammonium salts of lauric acid, myristic acid, palmitic acid, stearic acid, oleic acid, linoleic acid, ricinoleic acid, coconut fatty acid, palm kernel fatty acid and tallow fatty acid, as well as technical grade mixtures thereof which are frequently vended in the form of "soap noodles" which predominantly contain one or more of the aforesaid compounds, and which soap noodles may contain in further but minor amounts other additional constituents such as water, glycerine, inorganic salts (e.g., sodium chloride), as well as chelating agents, e.g. tetrasodium ethylene diamine tetraacetic acid.

The most preferred anionic surfactants are disclosed with reference to one or more of the examples. It is to be noted that such anionic surfactants may be added to the composition as a starting material, or may be formed in situ in the compositions, e.g. the reaction of an alkylsulphonic acid with a suitable species to form a water soluble or water dispersible salt therefrom.

With respect to the essential nonionic surfactant constituent, generally any nonionic surfactant material may be used in the inventive compositions as the essential nonionic surfactant. Practically any hydrophobic compound having a carboxy, hydroxy, amido, or amino group with a free hydrogen attached to the nitrogen can be condensed with an alkylene oxide, especially ethylene oxide or with the polyhydration product thereof, a polyalkylene glycol, especially polyethylene glycol, to form a water soluble or water dispersible nonionic surfactant compound. Exemplary useful nonionic surfactants include primary and secondary linear and branched alcohol alkoxylates, preferably ethoxylates, such as those based on $C_6$-$C_{18}$ alcohols which further include an average of from 2 to 80 moles of ethoxylation per mol of alcohol. Such include the Genapol® UD surfactants (ex. Clariant), C10 oxo-alcohol ethoxylates available under the Lutensol® ON tradename (ex BASF), ethoxylated aliphatic alcohols available in the Neodol® surfactant series, as well as under the Tomadol® tradename as well as the Genapol® tradename (ex. Clariant), with the formula $RO(CH_2CH_2O)_nH$ where R is the primary linear alcohol and n is the total number of moles of ethylene oxide, wherein R is typically between 6 and 22, and n typically a value of between 1 and 16. A further exemplary class of useful nonionic surfactants include polyalkylene oxide condensates of alkyl phenols. These compounds include the condensation products of alkyl phenols having an alkyl group containing from about 6 to 12 carbon atoms in either a straight chain or branched chain configuration with an alkylene oxide, especially an ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene and the like.

A further class of useful nonionic surfactants include alkoxy block copolymers, and in particular, compounds based on ethoxy/propoxy block copolymers. Polymeric alkylene oxide block copolymers include nonionic surfactants in which the major portion of the molecule is made up of block polymeric $C_2$-$C_4$ alkylene oxides. Such nonionic surfactants, while preferably built up from an alkylene oxide chain starting group, and can have as a starting nucleus almost any active hydrogen containing group including, without limitation, amides, phenols, thiols and secondary alcohols.

Most preferred nonionic surfactants include those based on linear or branched, alkoxylated alcohols such as those based on $C_6$-$C_{18}$ alcohols which further include an average of from 2 to 80 moles of ethoxylation per mol of alcohol.

While the total amount of the essential at least one nonionic surfactant may be present in any effective amounts, and amounts as little as 0.01% wt. to as much as about 10% wt. are contemplated, advantageously the total amount of the and preferably at least about 0.1% wt., and in order of increasing preference are at least about: 0.2, 0.25, 0.3, 0.4, 0.50, 0.6, 0.7, 0.75, 0.8, 0.9 and 1% wt. Concurrently advantageously the total amount of the necessary at least one nonionic surfactant is present in an amount of not more than 10% wt. and in order of increasing preference is not more than about: 9, 8, 7.5, 7, 6, 5, 4, 3, 2.75, 2.5, 2.25 and about 2% wt, based on the total weight of the composition.

While the total amount of the essential at least one anionic surfactant may be present in any effective amounts, and amounts as little as 0.01% wt. to as much as about 10% wt. are contemplated, advantageously the total amount of the and preferably at least about 0.1% wt., and in order of increasing preference are at least about: 0.5, 0.6, 0.7, 0.75, 0.8, 0.9, 1, 1.1, 1.2, 1.25, 1.3, 1.35, and 1.4% wt. Concurrently advantageously the total amount of the necessary at least one anionic surfactant is present in an amount of not more than 0% wt. and in order of increasing preference is not more than about: 9, 8, 7.5, 7, 6.5, 6, 5.5 and about 5% wt, based on the total weight of the composition.

It is to be noted that in preferred embodiments of the first and second aspects of the invention, the total amount of the one or more anionic surfactants is preferably not in excess of about 2.5% wt, and more preferably not in excess of about 2% wt., while in preferred embodiments of the third aspect of the invention the total amount of the one or more anionic surfactants is preferably at least about 2.5% wt, to about 7.5% wt, and preferably is from about 4% wt. to about 6% wt.

In certain preferred embodiments there is present both at least one nonionic surfactant concurrently and the at least one anionic surfactant is preferably included in excess of the least one nonionic surfactant, and advantageously the respective weight ratios of the at least one anionic surfactant:at least one nonionic surfactant is at least about 1.5:1, preferably at least about 2:1, and especially preferably at least about 2.5:1. Even higher respective ratios of at least one anionic surfactant:at least one nonionic surfactant may be used as well.

Optionally the compositions of the invention may include one or more further amphoteric and/or zwitterionic surfactants where such are provided in amounts which are not overly deleterious to the overall antimicrobial properties of the inventive compositions and which also do not deleteriously affect the suspension of the inorganic abrasive particulates which are present in the compositions. By way of non-limiting examples such include one or more of the following betaines; alkyl betaines, alkyl amidobetaines, aminopropionates, aminoglycinates, imidazolinium betaines and sulfobetaines, and amphoteric surfactants: alkylampho(mono)acetates, alkylampho(di)acetates, alkylampho(mono)propionates, and alkylampho(di)propionates, amphoteric surfactants include those which may be represented by the following general formula

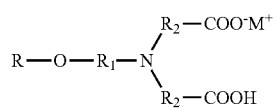

in which, R represents a $C_4$ to $C_{24}$ alkyl group, and is preferably a C10 to C16 alkyl group, R1 and R2 independently represent a $C_1$ to $C_8$ alkyl group, is preferably —$CH_2CH_2$— or —$CH_2CH_2CH_2$—, and M may be any salt-forming anion which permits water solubility or water miscibility of the compound, e.g., chloride, bromide, methosulfate, ethosulfate, lactate, saccharinate, acetate or phosphate.

When present such further amphoteric and/or zwitterionic surfactants may be present in any effective amount, which may be as little as 0.001% wt Generally however the amphoteric and/or zwitterionic surfactants do not exceed 10% wt. of the composition of which they form a part.

The cumlative amounts of the one or more surfactants which may be present in the compositions may be as little as about 0.01% wt. to about 15% wt., advantageously the cumulative amounts of the surfactants present in the inventive compositions in are in the range of about 1-10% wt. of the compositions.

Particularly preferred amounts, and the identity of surfactants are disclosed with reference to one or more of the examples.

As a further essential constituent, the inventive compositions necessarily comprise one or more inorganic abrasive particulate materials which are based on inorganic carbonate compounds. Preferred for use are inorganic carbonate compounds selected from: Group II alkali metal carbonates, magnesium carbonate, calcium carbonate, or calcium magnesium carbonate which are provided as discrete particulates having an average (maximum) particle size in the range from about 1 μm to about 1000 μm, preferably between about 10 μm to about 350 μm, and more preferably between about 50 μm and about 200 μm. In certain preferred embodiments, the inorganic particulate material necessarily comprise, consist essentially of, or consist of calcium carbonate. The inorganic carbonate is an abrasive material which is preferably present in amounts of between about 0.1% wt. to about 50% wt., preferably about 2-25% wt., preferably about 3-20% wt. of the inventive compositions of which they form a part.

While not essential to the invention, it is contemplated that a co-abrasive constituent may be additionally present to the essential one or more inorganic abrasive particulate materials based on inorganic carbonate compounds. Such a co-abrasive constituent may be one or more further particulate abrasive materials, examples of which include: oxides, carbonates, organic abrasive materials selected from polyolefins, polyethylenes, polypropylenes, polyesters, polystyrenes, acetonitrile-butadiene-styrene resins, melamines, polycarbonates, phenolic resins, epoxies and polyurethanes, natural materials selected from rice hulls, corn cobs, and the like, nepheline syenite, or talc and mixtures thereof. The particle size of such a co-abrasive constituent, when present, can range from about 1 μm to about 1000 μm, preferably between about 10 μm to about 200 μm, and more preferably between about 10 μm and about 100 μm. It is preferred to use those co-abrasive agents that will not scratch glass or ceramic surfaces.

As a further essential constituent of the first and second aspects of the invention are one or more gum based thickeners. Such gum based thickeners include exopolysaccharides (also known as biopolymers) such as welan gum, xanthan gum, rhamsan gum, gellan gum, dextran gum, pullulan gum, curdlan gum, and the like; marine gums such as agar, seagel, carrageenan, and the like; plant exudates, such as locust bean gum, gum arabic, gum Karaya, tragacanth, Ghatti, and the like; seed gums such as guar gum, locust bean gum, okra, psyllium, mesquite, and the like; as well as starch-based gums such as ethers, esters, and related derivatized compounds, e.g., gelatins, pectins, agars, carrageenans, locust beans, guars, xanthans, gellans and konjac gums. Particularly preferred is xantham gum, and in preferred embodiments xantham gum is the sole gum based thickener present in the compositions. The gum based thickener may exhibit any number average molecular weight range, such as 1000 to 1,000,000, and it may be present in any effective amount in order to provide both (a) a desired viscosity to the inventive compositions and to (b) provide an adequate degree of suspension of the inorganic abrasive particulate materials present in the composition, particularly subsequent to extended periods of storage of the composition and/or storage of the composition at elevated temperatures, e.g., at least 25° C., preferably at least 30° C., for periods of time. Such may be evaluated utilizing known-art testing protocols to approximate the storage stability of the inventive compositions. Advantageously the gum based thickener constituent is present in an amount of from about 0.001% wt., to about 7% wt., yet more preferably is comprises from about 0.05% wt-3% wt. of the composition. Further advantageously the gum based thickener constituent is also sufficiently stable at the alkaline conditions of the inventive compositions.

In certain preferred embodiments of the first aspect of the invention, the one or more gum based thickeners are the sole thickener constituents present in the inventive compositions and different conventional thickeners are expressly excluded. Such different conventional thickeners include thickeners based on naturally occurring or modified celluloses, e.g, cellulose, alkyl celluloses, alkoxy celluloses, hydroxy alkyl celluloses, polycarboxylate polymers, synthetic acrylic polymers such as polyacrylamides, and clays. Preferably, one or more of the aforesaid different conventional thickeners are excluded from compositions according to the first aspect of the invention.

According to the second aspect of the invention, in addition to the gum based thickener there is also necessarily present a clay based thickener, which comprise, for example, colloid-forming clays such as smectite and/or attapulgite types. The clay materials can be described as expandable layered clays, i.e., aluminosilicates and magnesium silicates. The term "expandable" as used to describe the instant clays relates to the ability of the layered clay structure to be swollen, or expanded, on contact with water. The expandable clays used herein are those materials classified geologically as smectites (or montmorillonite) and attapulgites (or polygorskites). Smectites are three-layered clays. There are two distinct classes of smectite-type clays. In the first, aluminum oxide is present in the silicate crystal lattice; in the second class of smectites, magnesium oxide is present in the silicate crystal lattice. The general formulas of these smectites are $Al_2(Si_2O_5)_2(OH)_2$ and $Mg_3(Si_2O_5)(OH)_2$, for the aluminum and magnesium oxide type clays, respectively. It is to be recognized that the range of the water of hydration in the above formulas may vary with the processing to which the clay has been subjected.

Commercially available clays include, for example, montmorillonite, bentonite, volchonskoite, nontronite, beidellite, hectorite, saponite, sauconite and vermiculite. The clays herein are available under various trade names such as Gelwhite GP, Gelwhite H, Mineral Colloid BP, and Laponite from Southern Clay Products, Inc., Texas; and Van Gel O from R. T. Vanderbilt. Gelwhite H-NF has a typical chemical analysis of $SiO_2$ 66.5%; $Al_2O_3$ 14.7%; MgO 3.2%; $Fe_2O_3$ 0.8%; CaO 2.2%; $Na_2O$ 3.3%; $K_2O$ 0.1%; $TiO_2$ 0.2%. Gelwhite L-NF has a typical chemical analysis of $SiO_2$ 66.5%; $Al_2O_3$ 14.7%; MgO 0.3.2%; $Fe_2O_3$ 0.8%; CaO 2.2%; $Na_2O$ 3.3%; $K_2O$ 0.1%; $TiO_2$ 0.2%. Gelwhite GP has a typical chemical analysis of $SiO_2$ 66.5%; $Al_2O_3$ 14.7%; MgO 3.2%; $Fe_2O_3$ 0.8%; CaO 2.2%; $Na_2O$ 3.3%; $K_2O$ 0.1%; $TiO_2$ 0.2%. Mineral Colloid BP has a typical chemical analysis of $SiO_2$ 62.9%; $Al_2O3$ 17.1%; MgO 2.4%; $Fe_2O_3$ 4.8%; CaO 0.7%; $Na_2O$ 2.1%; $K_2O$ 0.2%; $TiO_2$ 0.1%.

A second type of expandable clay material useful in the instant invention is classified geologically as attapulgite (polygorskite). Attapulgites are magnesium-rich clays having principles of superposition of tetrahedral and octahedral unit cell elements different from the smectites. A typical attapulgite analyses yields 55.02% $SiO_2$; 10.24% $Al_2O_3$; 3.53% $Fe_2O_3$; 10.45% MgO; 0.47% $K_2O$; 9.73% $H_2O$ removed at 150° C.; 10.13% $H_2O$ removed at higher temperatures. Like the smectites, attapulgite clays are commercially available. For example, such clays are marketed under the tradename Attagel, i.e. Attagel 40, Attagel 50 and Attagel 150 from Engelhard Minerals & Chemicals Corporation, as well as Veegum T which is described as being a magnesium aluminum silicate which is water washed natural smectite clay, and commercially available from R. T. Vanderbilt.

It is of course to be understood that two or more of each of the foregoing thickeners may be used to form the thickener constituent present in compositions of the second aspect of the invention. While both of the gum based thickener and a clay based thickener may be present in any effective amount in order to provide both (a) a desired viscosity to the inventive compositions and to (b) provide an adequate degree of suspension of the inorganic abrasive particulate materials present in the composition, particularly subsequent to extended periods of storage of the composition and/or storage of the composition at elevated temperatures, e.g, at least 25° C., preferably at least 30° C., for periods of time, advantageously the total amount of the thickener constituent is present in an amount of from about 0.001% wt., to about 7% wt., yet more preferably is comprises from about 0.05% wt-3% wt. of the composition. Further advantageously both the gum based thickener and the clay based thickener of the thickener constituent are also sufficiently stable at the alkaline conditions of the inventive compositions.

In certain preferred embodiments of the second aspect of the invention, the one or more gum based thickeners with the clay based thickener are the sole thickener constituents present in the inventive compositions and different conventional thickeners are expressly excluded. Such different conventional thickeners include thickeners based on naturally occurring or modified celluloses, e.g, cellulose, alkyl celluloses, alkoxy celluloses, hydroxy alkyl celluloses, polycarboxylate polymers, and synthetic acrylic polymers such as polyacrylamides, and clays. Preferably, one or more of the aforesaid different conventional thickeners are expressly excluded from compositions according to the second aspect of the invention.

According to the third aspect of the invention, the inventive compositions comprise an acrylate based thickener. Such include polyacrylate polymers including those sold under trade names Carbopol®, Acrysol® ICS-1 and Sokalan®. The preferred polymers are polyacrylates. Other monomers besides acrylic acid can be used to form these polymers including such monomers as ethylene and propylene which act as diluents, and maleic anhydride which acts as a source of additional carboxylic groups. Acrylate based thickeners include homopolymers of unsaturated, polymerizable carboxylic monomers such as acrylic acid, methacrylic acid, maleic acid, itaconic acid, maleic anhydride, and the like. Further useful acrylate based thickeners include hydrophobically modified polyacrylic acid polymers which include a large hydrophilic portion (the polyacrylic acid portion) and a hydrophobic portion (which can be derived from a long carbon chain acrylate ester). Representative higher alkyl acrylic esters are decycl acrylate, lauryl acrylate, stearyl acrylate, behenyl acrylate and melissyl acrylate, and the corresponding methacrylates. It should be understood that more than one carboxylic monomer and more than one acrylate ester or vinyl ester or ether or styrenic can be used in the monomer charge. The polymers can be dispersed in water and neutralized with base to thicken the aqueous composition, form a gel, or emulsify or suspend a deliverable. Examples of such hydrophobically modified polyacrylic acid polymers are sold as Carbopol® 1342 and 1382 and Pemulen® TR-1, TR-2, 1621, and 1622, all available from Noveon. The carboxyl containing polymers are prepared from monomers containing at least one activated vinyl group and a carboxyl group, and would include copolymers of polymerizable carboxylic monomers with acrylate esters, acrylamides, alkylated acrylamides, olefins, vinyl esters, vinyl ethers, or styrenics. The carboxyl containing polymers preferably have molecular weights greater than about 500 to as high as several billion, or more, usually greater than about 10,000 to 900,000 or more. Any of the forgoing polymers may be crosslinked to varying degrees.

Further, albeit non-limiting examples of useful acrylate thickeners include crosslinked copolymers of acrylates, (meth)acrylic acid, maleic anhydride, and various combinations thereof, including those available from Rheox Inc., Highstown, N.J. (such as Rheolate® 5000 polymer), 3 V Sigma, Bergamo, Italy (such as Stabelyn® 30 polymer, which is an acrylic acid/vinyl ester copolymer, or Polygel® and Synthalen® polymers, which are crosslinked acrylic acid polymers and copolymers), Noveon (such as Carbopol 674 (lightly crosslinked polyacrylate polymer), Carbopol 676 (highly crosslinked polyacrylate polymer), Carbopol EP-1 thickener, which is a acrylic emulsion thickener), or Rohm and Haas (such as Acrysol® ICS-1 and Aculyn® 22 thickeners, which are hydrophobically modified alkali-soluble acrylic polymer emulsions and Aculyn® 44 thickener, which is a hydrophobically modified nonionic polyol). A particularly preferred acrylate thickener is based on hydrophobically modified, alkali soluble acrylic polymers generally sold under the Acusol® tradename, such as Acusol® 823.

It is of course to be understood that two or more acrylate based thickeners may be used to form the thickener constituent present in compositions of the third aspect of the invention.

While the acrylate based thickener may be present in any effective amount in order to provide both (a) a desired viscosity to the inventive compositions and to (b) provide an adequate degree of suspension of the inorganic abrasive particulate materials present in the composition, particularly subsequent to extended periods of storage of the composition and/or storage of the composition at elevated temperatures, e.g, at least 25° C., preferably at least 30° C., for periods of time, advantageously the total amount of the thickener constituent present is in an amount of from about 0.001% wt., to about 7% wt., yet more preferably is comprises from about 0.05% wt-3% wt. of the composition. Further advantageously both the acrylate based thickener constituent are also sufficiently stable at the alkaline conditions of the inventive compositions.

In certain preferred embodiments of the third aspect of the invention, the one or more acrylate thickeners may be present with one or more further different conventional thickeners. Such different conventional thickeners include thickeners based on naturally occurring or modified celluloses, e.g, cellulose, alkyl celluloses, alkoxy celluloses, hydroxy alkyl celluloses, polycarboxylate polymers, and synthetic acrylic polymers such as polyacrylamides, and clays. In these preferred embodiments then, one or more acrylate thickeners is thus necessarily present with at least one further different conventional thickener.

In other preferred embodiments of the third aspect of the invention, the one or more acrylate thickeners are present to the exclusion of one or more of the foregoing recited further different conventional thickeners, and in certain such preferred embodiments all further of the foregoing recited further different conventional thickeners are excluded and the one or more acrylate thickeners are the sole constituents of the thickener constituent.

Preferably, one or more of the aforesaid different conventional thickeners are expressly excluded from compositions according to the third aspect of the invention.

The inventive compositions also necessarily comprise a non-cationic germicide constituent which has germicidal or antimicrobial efficacy against at least one of gram-positive or gram-negative pathogens, e.g., bacteria or other microorganisms. Such are one or more non-cationic antimicrobial compounds or constituents, which include one or more of: halogenated diphenyl ethers like 2,4,4-trichloro-2-hydroxydiphenyl ether (Triclosan or TCS), 2,2-dihydroxy-5,5-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl phenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m,m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4-chloro 2,4-dihydroxydiphenyl methane, 5-bromo 2,4-dihydroxydiphenyl methane, and 4-bromo 2,4-dihydroxydiphenyl methane, bisphenolic compounds like 2,2-methylene bis(4-chlorophenol), 2,2-methylene bis(3,4,6-trichlorophenol), 2,2-methylene bis(4-chloro-6-bromophenol), bis(2-hydroxy-3,5-dichlorophenyl) sulphide, and bis(2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4-trichlorocarbanilides (Triclocarban or TCC), 3-trifluoromethyl-4, 4-dichlorocarbanilide, 3,3,4-trichlorocarbanilide, etc.).

Of these, preferred are phenol based non-cationic microbicidals, especially those based on one or more phenolic compounds, particularly 2-hydroxydiphenyl compounds which may be exemplified by the following classes of compounds:

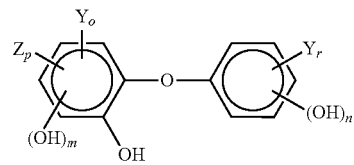

wherein Y is chlorine or bromine, Z is $SO_2H$, $NO_2$, or $C_1$-$C_4$ alkyl, r is 0 to 3, o is 0 to 3, p is 0 or 1, m is 0 or 1, and n is 0 or 1. In preferred embodiments, Y is chlorine or bromine, m is 0, n is 0 or 1, o is 1 or 2, r is 1 or 2, and p is 0, and according to especially preferred embodiments, Y is chlorine, m is 0, n is 0, o is 1, r is 2, and p is 0.

Particularly useful 2-hydroxydiphenyl compounds include those which may be represented by the structure:

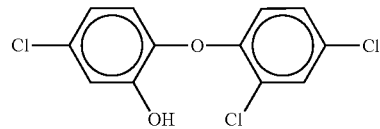

which is commonly referred to as "TRICLOSAN" and which is presently commercially available from Ciba Specialty Chemicals Corp., as well as halogenated carbanilides, e.g., TCC.

Further exemplary useful phenolic based disinfecting agents include 2,2'-hydroxy-5,5'-dibromo-diphenyl ether which may be represented by the structure:

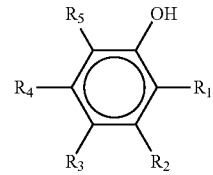

wherein $R_1$ is hydro, hydroxy, $C_1$-$C_4$ alkyl, chloro, nitro, phenyl, or benzyl; $R_2$ is hydro, hydroxy, $C_1$-$C_6$ alkyl, or halo; $R_3$ is hydro, $C_1$-$C_6$ alkyl, hydroxy, chloro, nitro, or a sulfur in the form of an alkali metal salt or ammonium salt; $R_4$ is hydro or methyl, and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid.

Still further useful phenol derivatives include those which may be represented by the structure:

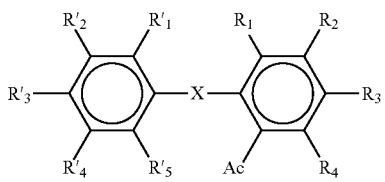

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine.

Preferred phenol derivatives useful in the germicide constituent include halophenols such 3-trifluoromethyl-4,4'-dichlorocarbanilide, 3,3',4-trichlorocarbanilide, as well as 2,4-dichloro-3,5-m-xylenol ("DCMX"). Phenol based non-cationic antimicrobials are preferred, of which parachlorometacresol ("PCMC") and especially parachlorometaxylenol ("PCMX"). The germicide constituent may be based, for example, on one or more phenol derivatives such as those based on 2-hydroxydiphenyl compounds, including Triclosan® (ex. Ciba), those based on 2,2'-hydroxy-5,5'-dibromo-diphenyl ethers, such as one or more of chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid, as well as further diphenol compounds such as hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine, and "Triclocarban", 3,4,4'-trichlorocarbanilide as well as derivatives thereof.

Particularly preferred as the non-cationic germicide constituent are one or more compounds selected from the group consisting of: parachlorometaxylenol, and halogenated carbanilides (e.g., 3,4,4'-trichlorocarbanilide (also referred to as Triclocarban® or TCC), 3-trifluoromethyl-4,4-dichlorocarbanilide, and 3,3,4-trichlorocarbanilide.

In certain preferred embodiments the non-cationic germicide constituent necessarily comprises, or consists essentially of, or consists of parachlorometaxylenol.

In certain preferred embodiments the non-cationic germicide constituent necessarily comprises, or consists essentially of, or consists of a halogenated carbanilide, and preferably 3,4,4'-trichlorocarbanilide.

The non-cationic germicide constituent may be present in any amount which is effective in the reduction of gram-positive and/or gram-negative pathogens, e.g., bacteria or other microorganisms, which may be measured according to recognized testing protocols. The non-cationic germicide constituent may be present in any effective amount, which may be as little as 0.001% wt., and in preferred embodiments the non-cationic germicide constituent comprises about 0.01% wt.-5% wt., more preferably comprises from about 0.25% wt, to about 3% wt., based on the total weight of the composition of which they form a part. Particularly preferred non-cationic germicide constituents and their amounts are disclosed with reference to one or more of the example compositions.

As the inventive compositions are highly aqueous in nature, they contain a significant amount of water. The water may be tap water, but is preferably distilled and is most preferably deionized water, or water provided by ultrafiltration and/or via a reverse osmosis filtration process in order to ensure the minimum likelihood of undesired impurities such as organics or inorganics, especially minerals salts, as well as undesired microorganisms within the water used to form the inventive compositions as such may undesirably interfere with the operation of the constituents present in the aqueous compositions according to the invention. Water is added to order to provide to 100% by weight of the compositions of the invention, and may form as little as about 50% wt. of the inventive compositions. Advantageously water forms between about 50% wt., preferably at least about 60% wt., yet more preferably at least about 70% wt., to about 95% wt., yet more preferably to about 90% wt. of the inventive compositions. Particularly preferred amounts of water are disclosed with reference to one or more of the example compositions.

The compositions are alkaline, and preferably have a pH of 7 or more, preferably a pH of between about 7.5-12, more preferably between about 8 and 11, yet more preferably have a pH of between about 8 and 10.5. The inventors had surprisingly discovered that when the pH of the inventive compositions were less than about 7, that the compositions exhibited unsatisfactory antimicrobial efficacy, and at the same time when the compositions were in excess of about 10.5, subsequent to extended and/or harsh storage conditions the compositions would undesirably split into two phases, and/or the inorganic abrasive particulate materials would undesirably flocculate in the composition.

The compositions of the invention are viscous, and exhibit a viscosity of between about 250 to about 3000 cPs at 25° C., preferably at least about 1000 cPs at 25° C., and particularly preferably in the range of about 1800-2400 cPs at 25° C.

In preferred embodiments the inventive compositions expressly exclude organic acids, e.g., citric, lactic, formic acids and other carboxylic acids which would impart an acid pH to the compositions, as well as inorganic acids and mineral acids, e.g., hydrochloric acid, sulfuric acid, and the like which would also impart an acid pH to the compositions.

An exception to the foregoing preferential inclusion of acids is made wherein one or more acids, preferably one or more organic acids is included in the composition as a precursor to a surfactant which is formed in situ in the compositions of the invention. One such acid is and alkyl-sulphamic acid which when reacted (e.g., neutralized) with a base such as sodium hydroxide forms an anionic surfactant species, and any remaining unreacted alkylsulphamic acid may be present in minor amounts, preferably not more than about 0.05% wt., more preferably not more than about 0.02% wt. of the inventive compositions. Most preferably if initially added as a surfactant precursor constituent, any such organic acids are consumed by the reaction used to form one or more of the surfactant constituents.

The inventive compositions may include minor amounts of, typically about 0-15% wt. of one or more optional constituents for improving the technical and/or aesthetic characteristics of the invention. Such further optical constituents may for example include: fragrances, dyestuffs, builders, pH adjusting agents and pH buffers including organic and inorganic salts, opacifiers, organic solvents, builders, hydrotropes (particularly as a solubilizing agent for a fragrance constituent) anti-oxidants, preservatives, and anti-corrosion agents and the like. Such may be present in any effective amounts, which cumulatively typically do not exceed about 15% wt. of the inventive compositions, and preferably do not exceed about 10% wt. of the compositions.

The inventive compositions may optionally include an organic solvent constituent, and according to the fourth aspect of the invention, such one or more organic solvents are necessarily present as a further essential constituent. Such organic solvent s may be included in order to aid in the solubilization of one or more further constituents in the largely aqueous compositions of the invention. By way of non-limiting example, useful organic solvents include alcohols including lower alkyl aliphatic monohydric alcohols, glycols, acetates, ether acetates, glycerols, as well as polyethylene glycols and glycol ethers. Mixtures of these further optional organic solvents can also be used. Non-limiting examples of useful alcohols include $C_1$-$C_6$ monohydric alcohols, primary, secondary and tertiary alcohols, such as methanol, ethanol, and the various isomers of propanol and butane. Non-limiting examples of useful glycol ethers and examples include those glycol ethers having the general structure $R_a$—O—[$CH_2$—CH(R)—($CH_2$)$_a$—O]$_n$—H, wherein $R_a$ is $C_{1-20}$ alkyl or alkenyl, or a cyclic alkane group of at least 6 carbon atoms, which may be fully or partially unsaturated or aromatic; n is an integer from 1 to 10, preferably from 1 to 5; each R is selected from H or $CH_3$; and a is the integer 0 or 1. Specific and preferred solvents are selected from propylene glycol methyl ether, dipropylene glycol methyl ether, tripropylene glycol methyl ether, propylene glycol n-propyl ether, ethylene glycol n-butyl ether, diethylene glycol n-butyl ether, diethylene glycol methyl ether, propylene glycol, ethylene glycol, diethylene glycol monoethyl ether acetate and the like. Particularly preferred organic solvents are disclosed with reference to the Examples. When present such further optional one or more organic solvents may advantageously be present in any effective amount, preferably in amounts of between about 0.001-10% wt., and preferably between about 0.01-5% wt. based on the total weight of the inventive composition of which they form a part.

The compositions of the invention optionally but preferably include an effective amount of a pH adjusting agent and/or a pH buffer, which is used to provide and/or maintain the alkaline pH of the compositions. In preferred embodiments a pH adjusting agent and/or a pH buffer is a further essential constituent of the invention. Essentially any material which may be used to impart alkalinity of the inventive compositions are expected to be useful in the compositions. Non-limiting examples of such include one or more of: caustics, basic compositions such as alkali metal hydroxides, alkaline earth and alkali metal phosphates, polyphosphates, pyrophosphates, triphosphates, tetraphosphates, silicates, metasilicates, aluminosilicates (zeolites), borates, aluminates, polysilicates, carbonates, hydroxides, and mixtures of the same. Further exemplary and useful pH adjusting constituents include organic compounds such as monoalkanolamines, dialkanolamines, trialkanolamines, and alkylalkanolamines such as alkyl-dialkanolamines, and dialkyl-monoalkanolamines. The alkanol and alkyl groups are generally short to medium chain length, that is, from 1 to 7 carbons in length. For di- and trialkanolamines and dialkyl-monoalkanolamines, these groups can be combined on the same amine to produce for example, methylethylhydroxypropylhydroxylamine. One of ordinary skill in the art can readily ascertain other members of this group. Preferred alkanolamines include monoethanolamine. Particularly preferred pH adjusting agent and/or a pH buffer materials are disclosed with reference to one or more of the Examples. The inventors have found that the use of sodium borate and monoethanolamine as a pH adjusting agents provided good pH stability even under harsh storage conditions, however it was surprisingly noted that the use of sodium borate provided the best retention of the original color of the composition following an extended period of storage at elevated temperatures. Such is discussed with reference to certain of the Examples. When present, and in certain embodiments it is understood that the pH adjusting agent and/or a pH buffer is a further essential constituent of the invention, the pH adjusting agent and/or a pH buffer is present in any effective amount in order to provide an alkaline pH and/or to maintain the alkalinity of the inventive compositions. Such may be present in amount of as little as about 0.001% wt. to about 5% wt., but preferably the pH adjusting agent and/or a pH buffer is present in an amount of from about 0.1-2% wt., based on the total weight of the inventive composition of which it forms a part.

The compositions of the invention may optionally include a fragrance constituent, which may be based on natural and/or synthetic fragrances and most commonly are mixtures or blends of a plurality of such fragrances, optionally in conjunction with a carrier such as an organic solvent or a mixture of organic solvents in which the fragrances are dissolved, suspended or dispersed. Such may be natural fragrances, e.g, natural extracts of plants, fruits, roots, stems, leaves, wood extracts, e.g. terpineols, resins, balsams, animal raw materials, e.g., civet and beaver, as well as typical synthetic perfume compounds which are frequently products of the ester, ether, aldehyde, ketone, alcohol and hydrocarbon type, e.g., benzyl acetate, linalyl acetate, citral, citronellal, methyl cedryl ketone, eugenol, isoeugenol, geraniol, linalool, and Typically it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. When present in a pressurized, sprayable treatment composition, in accordance with certain of the preferred embodiments, the fragrance constituent may be present in any effective amount such that it can be discerned by a consumer of the composition, however such is advantageously present in amounts of up to about 1% wt., preferably are present in amounts of from about 0.00001% wt. to about 0.5% wt., and most preferably is present in an amount of from about 0.0001% wt. to 0.5% wt. based on the total weight of the treatment composition of which it forms a part.

A further optional constituent of pressurized, sprayable treatment compositions of the invention include colorant, such as dyes and pigments which may be used to impart a color to the compositions of which they form a part.

The treatment compositions of the invention may also optionally include a preservative constituent which is used to control undesired microorganisms within the treatment composition particularly when the treatment composition is in long-term storage and at elevated temperatures. While these are normally not present due to the microbicidal efficacy of the compositions as taught herein, such ancillary preservative constituents may be included in minor but effective amounts. Nonlimiting examples include one or more of parabens, including methyl parabens and ethyl parabens, glutaraldehyde, formaldehyde, 2-bromo-2-nitropropoane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. Further exemplary useful preservatives include those which are commercially including a mixture of 5-chloro-2-methyl-4-isothiazolin-3-one and 2-methyl-4-isothiazolin-3-one marketed under the trademark KATHON® CG/ICP as a preservative composition presently commercially available from Rohm and Haas (Philadelphia, Pa.).

While the inventive compositions can be provided and stored in a non-deformable bottle but more preferably is provided in a squeezable container, such as a tube or deformable bottle fitted with a flow directing nozzle which provides for easy dispensing of the composition by the consumer directly onto hard surfaces. The container may also be I the form of a resealable container from which the inventive composition may be poured and thereafter the container resealed, e.g, a bottle or jar. A preferred container is a manually deformable bottle formed from a synthetic polymeric material, e.g, a polyolefin (e.g, PE, LDPE, LLDPE, HDPE, PP) polyamide, polycarbonate or blend of two or more synthetic polymers, which container may be used to contain an store a quantity of the inventive composition, which container is also provided with a dispensing cap or dispensing nozzle, through which a quantity of the inventive composition may be dispensed from the interior of the container and onto a hard surface in need of a cleaning treatment, and/or wherein the presence of undesirable microorganisms is known or suspected.

The inventive compositions are particularly useful in the treatment of inanimate surfaces in order to impart a cleaning effect thereto, as well as a microbicidal benefit (e.g, disinfecting, sanitizing) thereto. Inanimate surfaces include hard surfaces, which are typically nonporous hard surfaces. By way of example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted are lavatory fixtures, lavatory appliances (toilets, bidets, shower stalls, bathtubs and bathing appliances), wall and flooring surfaces especially those which include refractory materials and the like. Further hard surfaces which are particularly denoted are those associated with kitchen environments and other environments associated with food preparation. Hard surfaces also include those associated with hospital environments, medical laboratories and medical treatment environments.

The viscous nature of the composition provides excellent and generally uniform coverage to any inclined surfaces to which it has been applied. Advantageously such an applied composition forms a lamina which coats the inclined surface and due to excellent retention on such inclined surface, the composition may be used to very effectively clean and impart an antimicrobial benefit to the coated inclined surface.

The abrasive constituent of the compositions also provide for an abrasive benefit for improved cleaning of treated surface, which may optionally be manually cleaned by a user, e.g., with a sponge, a paper towel, a fibrous wipe or a brush.

It has been surprisingly observed that preferred compositions of the invention not only provide excellent cleaning and antimicrobial benefits to treated surfaces, but also that the compositions are storage stable and do not suffer from separation into two or more phases and/or undergo undesired amounts of flocculation of the abrasive constituent present in the compositions, even under long term storage at elevated temperatures. Such is believed attributable to the specific amounts of the thickener constituents present, their respective ratios, and the controlled amounts of the remaining constituents, including the limited amounts of specified surfactants, which is achieved even in the alkaline treatment compositions provided by the invention.

The following examples exhibit exemplary and preferred formulations of the invention. It is to be understood that these examples are provided by way of illustration only and that further useful formulations falling within the scope of the present invention and the claims may be readily produced by one skilled in the art without deviating from the scope and spirit of the invention.

EXAMPLES

Formulations according to the invention were produced by mixing the constituents outlined in Table 1 by adding the individual constituents into a beaker of water at room temperature which was stirred with a conventional magnetic stirring rod. Stirring continued until each of the formulations were homogenous in appearance. It is to be noted that the constituents might be added in any order, but it is preferred that a major proportion of water be the initial constituent provided to a mixing vessel or apparatus as it is the major constituent and addition of the further constituents thereto is convenient. Still more preferably to a major part of the water which is maintained under constant stirring are added the constituents are added with a sufficient time lapse between the addition of each constituent in order to ensure that the immediately prior added constituent has been homogenously blended. After the addition of the final constituent, mixing continued for 5-60 minutes to ensure homogenous blending.

These compositions according to the examples are indicated on Table 1 by the letter "E" followed by a digit.

Certain compositions which are considered to be "comparative examples" were also produced in the manner described above and using the same constituents, and these comparative examples are indicated on Table 2, following. These compositions according to the comparative examples are indicated by the letter "C" followed by a digit.

TABLE 1

| | E1 | E2 | E3 | E4 | E5 | E6 | E7 | E8 |
|---|---|---|---|---|---|---|---|---|
| sodium lauryl sulfate (28%) | 5.0 | 5.0 | 5.0 | 5.0 | — | — | — | — |
| alcohol ethoxylate (99.5%) | 1.0 | 1.0 | 1.0 | 1.0 | 1.0 | 1.0 | 1.0 | 1.0 |

TABLE 1-continued

| | | | | | | | | |
|---|---|---|---|---|---|---|---|---|
| PCMX (98%) | 1.0 | 1.0 | 1.0 | 1.0 | 2.4 | 1.0 | 0.8 | 0.5 |
| particulate carbonate (94.5%) | 15.0 | 15.0 | 15.0 | 15.0 | — | — | — | — |
| calcium magnesium carbonate (95%) | — | — | — | — | 15.0 | 15.0 | 15.0 | 15.0 |
| xanthan gum (98%) | 0.6 | 0.6 | 0.6 | 0.6 | 0.6 | 0.6 | 0.6 | 0.6 |
| magnesium aluminum silicate | — | — | — | — | 0.1 | — | — | — |
| alkylsulphonic acid (96%) | — | — | — | — | 1.2 | 1.2 | 1.2 | 1.2 |
| propylene glycol | 2.0 | 2.0 | 2.0 | 2.0 | 5.0 | 2.0 | 2.0 | 2.0 |
| monoethanolamine (90%) | — | 0.5 | — | 0.5 | — | — | — | — |
| sodium hydroxide | — | — | — | — | 0.6 | 0.6 | 0.6 | 0.6 |
| sodium borate (98%) | 0.5 | — | 0.5 | — | — | — | — | — |
| fragrance1 | 0.2 | 0.2 | — | — | 0.2 | 0.2 | 0.2 | 0.2 |
| fragrance2 | — | — | 0.2 | 0.2 | — | — | — | — |
| preservative | 0.05 | 0.05 | 0.05 | 0.05 | — | — | — | — |
| RO water | q.s. | q.s. | q.s. | q.s. | q.s. | q.s. | q.s. | q.s. |

| | E9 | E10 | E11 | E12 | E13 | E14 | E15 |
|---|---|---|---|---|---|---|---|
| sodium lauryl sulfate (28%) | — | — | 17.85 | — | 5.0 | 5.0 | 5.0 |
| alcohol ethoxylate (99.5%) | 1.0 | 1.0 | 2.0 | 2.0 | 1.0 | 1.0 | 1.0 |
| PCMX (98%) | 1.0 | 1.0 | 1.0 | 1.0 | 1.0 | 1.0 | 1.0 |
| particulate carbonate (94.5%) | 15.0 | 15.0 | 13.0 | 13.0 | 15.0 | 15.0 | 15.0 |
| calcium magnesium carbonate | — | — | — | — | — | — | — |
| xanthan gum (98%) | 0.6 | 0.6 | — | — | 0.6 | 0.6 | 0.6 |
| magnesium aluminum silicate | — | 0.3 | — | — | 0.3 | — | — |
| acrylate thickener | — | — | 0.4 | 0.4 | — | — | — |
| alkylsulphonic acid (96%) | 1.2 | 1.2 | — | 1.2 | — | — | — |
| propylene glycol | 2.0 | 2.0 | — | — | 2.0 | 2.0 | 2.0 |
| monoethanolamine (90%) | — | — | — | — | — | — | — |
| sodium hydroxide | 0.6 | 0.6 | — | 0.6 | — | — | — |
| sodium borate (98%) | — | — | — | — | — | — | — |
| sodium carbonate (98%) | — | — | 5.0 | 5.0 | 5.0 | 5.0 | — |
| fragrance1 | 0.2 | 0.2 | 0.2 | 0.2 | 0.2 | 0.2 | 0.2 |
| fragrance2 | — | — | — | — | — | — | — |
| preservative | 0.05 | 0.05 | 0.02 | 0.02 | 0.05 | 0.05 | 0.05 |
| RO water | q.s. | q.s. | q.s. | q.s. | q.s. | q.s. | q.s. |

The following table identifies the individual constituents described in the foregoing examples. The constituents were used "as supplied" from their respective suppliers and may constitute less than 100% wt. "actives" in which case the amount is indicated in parenthesis, or may have been supplied as constituting 100% wt. "active" of the named compound, as indicated in the following Table.

TABLE 2

| | |
|---|---|
| sodium lauryl sulfate (28%) | anionic surfactant, sodium lauryl sulfate (28% wt. active) supplied as Empicol LX 28 (ex. Huntsman Co.) |
| alcohol ethoxylate (99.5% minimum) | nonionic surfactant, linear alcohol ethoxylate, (99.5% wt. active) supplied as Rokanol L10 (ex. Rokita SA) |
| PCMX (98% minimum) | parachlorometaxylenol (98% wt. active) (ex. Thomas Swan & Co., Ltd.) |
| particulate carbonate (94.5% minimum) | supplied as Kulubrite 15 (94.5% wt. active) (150 micrometers avg. particle size) |
| calcium magnesium carbonate (95% minimum) | supplied as comminuted particulate dolomite particles |
| xanthan gum (98% minimum) | supplied as Hydrocol CG (98% wt. active) (ex. Shangdong Fufeng Fermentation Co., Ltc.) |
| magnesium aluminum silicate | magnesium aluminum silicate, (100% wt. active) supplied as Veegum T (ex. R. T. Vanderbilt) |
| propylene glycol | propylene glycol, laboratory grade (ex. DOW Chem. Co.) |
| nonoethanolamine (90% minimum) | laboratory grade monoethanolamine (90% wt. active) as pH adjusting agent |
| sodium hydroxide | laboratory grade sodium hydroxide (100% wt. actives) |
| sodium borate (98% minimum) | supplied as hydrated borax (98% wt. active) (ex. Searles Valley Minerals) as pH adjusting agent |
| Fragrance1 | lavender fragrance, proprietary composition of its supplier |
| Fragrance2 | pine-type fragrance, proprietary composition of its supplier |
| preservative | supplied as Acticide BW 20, used as supplied |
| RO water | purified water via reverse osmosis |

The compositions of E1 and E2 demonstrated good storage stability and good antimicrobial efficacy when tested as demonstrated by the following.

Storage Stability Testing

The visual appearance (perceived viscosity, color), fragrance, specific gravity "SG", pH and viscosity, of the E1-E4 compositions were tested both initially ("as mixed") and at periodic weekly intervals thereafter, with separate aliquots of the E1-E4 compositions being stored at different temperatures. The separate aliquots of the E1-E4 compositions were stored at one of the following temperatures: −20° C., 5° C., 25° C., 40° C., 50° C., and 60° C. over the span of one to several weeks. At the time intervals indicated on Table 3, a sample was removed from the indicated storage temperature, allowed to equilibrate to room temperature (25° C.) and thereafter tested, with the indicated results reported on the table. The color, and appearance of the samples were visually observed and noted with an initial aliquot of the composition used as a comparative reference, and a reported result of "good" indicated parity with the reference sample, whereas "off-white" indicated a visible reduction in sample appearance as compared to the reference. The fragrance was evaluated by smelling the tested composition and comparing it with an initial aliquot of the composition; the substantivity of the reference aliquot was assigned a rating "5" and the fragrance was tested for relative substantivity on a scale of "5 to 0", with a "5" rating assigned to those tested formulations which were considered to have parity with the reference sample to the other extreme of the scale wherein "0" is assigned to a tested sample having no perceived fragrance. It is to be noted that a sample of each of the E1-E4 compositions was subjected to a freeze-thaw cycle (indicated as storage condition ("−20° C.") wherein the sample was completely frozen, stored for the indicated time interval, thereafter allowed to thaw and allowed to equilibrate to room temperature (25° C.) for 12-24 hours and thereafter tested, with the indicated results reported on the table. The results were averaged and reported on the following Table 3.

TABLE 3

| | storage temperature | | | | | |
|---|---|---|---|---|---|---|
| | −20° C. | 5° C. | 25° C. | 40° C. | 50° C. | 60° C. |
| E1 Initial (as mixed) | | | | | | |
| appearance | — | — | good | — | — | — |
| color | — | — | good | — | — | — |
| fragrance | — | — | 5 | — | — | — |
| pH at 25° C. | — | — | 8.85 | — | — | — |
| viscosity (cPs) | — | — | 1850 | — | — | — |
| SG | — | — | 1.12 | — | — | — |
| Week 1 | | | | | | |
| appearance | good | good | good | good | good | good |
| color | good | good | good | good | good | good |
| fragrance | 5 | 5 | 5 | 5 | 5 | 5 |
| pH at 25° C. | 8.81 | 8.82 | 8.1 | 8.69 | 8.64 | 8.54 |
| viscosity (cPs) | 2500 | 2200 | 2420 | 2480 | 2475 | 2385 |
| SG | — | 1.0979 | 1.1104 | 1.1290 | 1.1161 | 1.1222 |
| Week 3 | | | | | | |
| appearance | good | good | good | good | good | — |
| color | — | good | good | good | good | — |
| fragrance | — | 5 | 5 | 4 | 4 | — |
| pH at 25° C. | — | 8.78 | 8.61 | 8.58 | 8.56 | — |
| viscosity (cPs) | — | 2120 | 2500 | 2400 | 2460 | — |
| SG | — | 1.1113 | 1.1112 | 1.1177 | 1.1247 | — |
| Week 6 | | | | | | |
| appearance | — | good | good | good | good | — |
| color | — | good | good | good | good | — |
| fragrance | — | 5 | 5 | 4 | 3 | — |
| pH at 25° C. | — | 8.76 | 8.66 | 8.62 | 8.60 | — |
| viscosity (cPs) | — | 2050 | 2570 | 2495 | — | — |
| SG | — | 1.11 | 1.11 | .1.12 | 1.12 | — |
| Week 12 | | | | | | |
| appearance | — | good | good | good | — | — |
| color | — | good | good | good | — | — |
| fragrance | — | 5 | 4 | 3 | — | — |
| pH at 25° C. | — | 8.71 | 8.63 | 8.57 | — | — |
| viscosity (cPs) | — | 2190 | 2485 | 2430 | — | — |
| SG | — | 1.11 | 1.11 | 1.11 | — | — |

"—" indicated that the sample was not tested

| E2 Initial (as mixed) | | | | | | |
|---|---|---|---|---|---|---|
| appearance | — | — | good | — | — | — |
| color | — | — | good | — | — | — |
| fragrance | — | — | 5 | — | — | — |
| pH at 25° C. | — | — | 10.51 | — | — | — |
| viscosity (cPs) | — | — | 1985 | — | — | — |
| SG | — | — | 1.15 | — | — | — |
| Week 1 | | | | | | |
| appearance | good | good | good | good | good | good |
| color | good | good | good | good | good | good |
| fragrance | 5 | 5 | 5 | 5 | 5 | 5 |

TABLE 3-continued

| | storage temperature | | | | | |
|---|---|---|---|---|---|---|
| | −20° C. | 5° C. | 25° C. | 40° C. | 50° C. | 60° C. |
| pH at 25° C. | 10.96 | 10.67 | 10.67 | 10.56 | 10.56 | 10.59 |
| viscosity (cPs) | 2435 | 2100 | 2050 | 2015 | 2015 | 1995 |
| SG | — | 1.0975 | 1.1145 | 1.1117 | 1.1206 | 1.1215 |
| | | | Week 3 | | | |
| appearance | — | good | good | good | good | — |
| color | — | good | good | good | off-white | — |
| fragrance | — | 5 | 5 | 4 | 4 | — |
| pH at 25° C. | — | 10.56 | 10.48 | 10.32 | 10.44 | — |
| viscosity (cPs) | — | 2045 | 2115 | 2075 | 1975 | — |
| SG | — | 1.1081 | 1.1214 | 1.1228 | 1.1169 | — |
| | | | Week 6 | | | |
| appearance | — | good | good | good | good | — |
| color | — | good | off-white | off-white | off-white | — |
| fragrance | — | 5 | 5 | 4 | 3 | — |
| pH at 25° C. | — | 10.6 | 1058 | 10.52 | 10.47 | — |
| viscosity (cPs) | — | 2095 | 2080 | 2065 | 2150 | — |
| SG | — | 1.11 | 1.12 | 1.12 | 1.12 | — |
| | | | Week 12 | | | |
| appearance | — | good | good | good | — | — |
| color | — | off-white | off-white | off-white | — | — |
| fragrance | — | 4 | 4 | 3 | — | — |
| pH at 25° C. | — | 10.62 | 10.6 | 10.52 | — | — |
| viscosity (cPs) | — | 2025 | 2065 | 1990 | — | — |
| SG | — | — | — | — | — | — |

"—" indicated that the sample was not tested

E3
Initial (as mixed)

| | −20° C. | 5° C. | 25° C. | 40° C. | 50° C. | 60° C. |
|---|---|---|---|---|---|---|
| appearance | — | — | good | — | — | — |
| color | — | — | good | — | — | — |
| fragrance | — | — | 5 | — | — | — |
| pH at 25° C. | — | — | 8.9 | — | — | — |
| viscosity (cPs) | — | — | 1950 | — | — | — |
| SG | — | — | 1.08 | — | — | — |
| | | | Week 1 | | | |
| appearance | good | good | good | good | good | good |
| color | good | good | good | good | good | good |
| fragrance | 5 | 5 | 5 | 5 | 5 | 5 |
| pH at 25° C. | 8.74 | 8.73 | 8.66 | 8.61 | 8.58 | 8.58 |
| viscosity (cPs) | 2480 | 2135 | 2000 | 2460 | 2430 | 2425 |
| SG | 1.0858 | 1.1225 | 1.1224 | 1.0960 | 1.0956 | 1.0879 |
| | | | Week 3 | | | |
| appearance | — | good | good | good | good | — |
| color | — | good | good | good | good | — |
| fragrance | — | 5 | 5 | 4 | 4 | — |
| pH at 25° C. | — | 8.69 | 8.57 | 8.55 | 8.52 | — |
| viscosity (cPs) | — | 2215 | 2250 | 2430 | 2425 | — |
| SG | — | 1.12 | 1.12 | 1.11 | 1.10 | — |
| | | | Week 6 | | | |
| appearance | — | good | good | good | good | — |
| color | — | good | good | good | off-white | — |
| fragrance | — | 5 | 5 | 4 | 3 | — |
| pH at 25° C. | — | 8.71 | 8.65 | 8.50 | 8.49 | — |
| viscosity (cPs) | — | 2270 | 2295 | 2495 | 2500 | — |
| SG | — | 1.12 | 1.12 | 1.11 | 1.10 | — |
| | | | Week 12 | | | |
| appearance | — | good | good | good | — | — |
| color | — | good | good | off-white | — | — |
| fragrance | — | 5 | 4 | 3 | — | — |
| pH at 25° C. | — | 8.69 | 8.66 | 8.53 | — | — |

TABLE 3-continued

| | storage temperature | | | | | |
|---|---|---|---|---|---|---|
| | −20° C. | 5° C. | 25° C. | 40° C. | 50° C. | 60° C. |
| viscosity (cPs) | — | 2195 | 2260 | 2400 | — | — |
| SG | — | 1.12 | 1.11 | 1.11 | — | — |

"—" indicated that the sample was not tested

E4
Initial (as mixed)

| | −20° C. | 5° C. | 25° C. | 40° C. | 50° C. | 60° C. |
|---|---|---|---|---|---|---|
| appearance | — | — | good | — | — | — |
| color | — | — | good | — | — | — |
| fragrance | — | — | 5 | — | — | — |
| pH at 25° C. | — | — | 10.99 | — | — | — |
| viscosity (cPs) | — | — | 1875 | — | — | — |
| SG | — | — | 1.08 | — | — | — |

Week 1

| | −20° C. | 5° C. | 25° C. | 40° C. | 50° C. | 60° C. |
|---|---|---|---|---|---|---|
| appearance | phase separation | good | good | good | good | good |
| color | good | good | good | good | good | good |
| fragrance | 5 | 5 | 5 | 5 | 5 | 5 |
| pH at 25° C. | — | 10.6 | 10.62 | 10.60 | 10.68 | 10.57 |
| viscosity (cPs) | — | 2085 | 2055 | 2090 | 2110 | 2170 |
| SG | — | 1.0830 | 1.0822 | 1.0858 | 1.0883 | 1.0915 |

Week 3

| | −20° C. | 5° C. | 25° C. | 40° C. | 50° C. | 60° C. |
|---|---|---|---|---|---|---|
| appearance | — | good | good | good | good | — |
| color | — | good | off-white | off-white | off-white | — |
| fragrance | — | 5 | 5 | 4 | 4 | — |
| pH at 25° C. | — | 10.49 | 10.47 | 10.44 | 10.47 | — |
| viscosity (cPs) | — | 2110 | 2060 | 2070 | 2090 | — |
| SG | — | 1.11 | 1.11 | 1.1 | 1.11 | — |

Week 6

| | −20° C. | 5° C. | 25° C. | 40° C. | 50° C. | 60° C. |
|---|---|---|---|---|---|---|
| appearance | — | good | good | good | good | — |
| color | — | good | off-white | off-white | off-white | — |
| fragrance | — | 5 | 5 | 4 | 3 | — |
| pH at 25° C. | — | 10.56 | 10.53 | 10.54 | 10.49 | — |
| viscosity (cPs) | — | 2155 | 2120 | 2095 | 2005 | — |
| SG | — | 1.11 | 1.11 | 1.1 | 1.11 | — |

Week 12

| | −20° C. | 5° C. | 25° C. | 40° C. | 50° C. | 60° C. |
|---|---|---|---|---|---|---|
| appearance | — | good | good | good | — | — |
| color | — | off-white | off-white | off-white | — | — |
| fragrance | — | 5 | 4 | 3 | — | — |
| pH at 25° C. | — | 10.52 | 10.49 | 10.38 | — | — |
| viscosity (cPs) | — | 2085 | 2030 | 1975 | — | — |
| SG | — | 1.11 | 1.12 | 1.10 | — | — |

"—" indicated that the sample was not tested, also, due to phase separation ("splitting") of the −20° C. sample which was thus not subjected to further tests As is clearly understood from the reports resulted from Table 3, preferred compositions of the invention exhibited excellent retention of viscosity and specific gravity even under adverse storage conditions for multiple weeks, including at high temperatures. Preferred compositions also were phase stable, viz., did not split into two or more phases during or after the testing. Additionally when visually observed the preferred compositions appeared to retain reasonably good color and fragrance characteristics, and, most of the tested compositions appeared to a visual observer be thick and sufficiently viscous when poured from a container, which is substantiated by generally excellent retention of viscosity and specific gravity and suspension of the abrasives within the composition.

Antimicrobial Efficacy:

The antimicrobial efficacy of compositions E1, E2 and E5-E7 as described with reference to Table 1 were evaluated according to SANS 1615-2011 (South Africa National Standard) without dilution, against the following challenge organism: *Pseudomonas aeruginosa* (ATCC 15442 Pse 16), *Escherichia coli* (ATCC 8739 Esc 20) and *Staphylococcus aureus* (ATCC 6538 Sta 10) according to the recited test protocols, which specifically included: dilution of tested samples was "as is", testing temperature was 22° C., diluent for test solutions was a sterile hard water at 250 ppm hardness containing 1% skimmed milk, the exposure times were 5 minutes, the loading of the challenge organisms was approx. $10^5$ organisms per ml of the test solution, a suitable fluid inactivator was used to stop the test, and the counting medium was laboratory grade nutrient agar. The results of this testing are reported on Table 4.

TABLE 4

| | % inactivation (kill), 5 minute contact time | | |
|---|---|---|---|
| | *Pseudomonas aeruginosa* | *Escherichia coli* | *Staphylococcus aureus* |
| E1 | 99.9 | 99.9 | 99.9 |
| E2 | 99.9 | 99.9 | 99.9 |
| E5 | 99.9 | 99.9 | 99.9 |
| E6 | 99.9 | 99.9 | 99.9 |
| E7 | 99.9 | 99.9 | 99.9 |

As is seen from the foregoing each of the tested compositions exhibited good microbicidal efficacy.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An aqueous alkaline, storage stable, abrasive containing hard surface treatment composition which concurrently provides a cleaning and a sanitizing and/or disinfecting benefit to hard surface, wherein the composition comprises:
   0.01-15% wt. of at least one anionic surfactant and at least one nonionic surfactant, and wherein the amount of the at least one anionic surfactant is in excess of the amount of the at least one nonionic surfactant;
   0.1-50% wt. of one or more inorganic abrasive particulate materials which are based on inorganic carbonate compounds;
   a gum based thickener;
   at least one non-cationic germicide constituent, which is one or more compounds selected from the group consisting of: parachlorometaxylenol, and halogenated carbanilides;
   at least 50% wt. of water;
   0.001-5% wt. of sodium borate as a pH adjusting agent and/or a pH buffer;
   wherein the composition exhibits a pH in the range of 7-10.5, and exhibits a viscosity of 1000-3000 cPs, when measured at 25° C.; and,
   wherein the composition exhibits a retention of initial color of the composition which is parity with a sample of the composition subsequent to 6 weeks storage at 40 deg.C.

2. An aqueous alkaline, storage stable, abrasive containing hard surface treatment composition which concurrently provides a cleaning and a useful sanitizing and/or disinfecting benefit to a hard surface wherein the composition comprises:
   0.01-15% wt. of at least one anionic surfactant and at least one nonionic surfactant, and wherein the amount of the at least one anionic surfactant is in excess of the amount of the at least one nonionic surfactant;
   0.1-50% wt. of one or more inorganic abrasive particulate materials which are based on inorganic carbonate compounds;
   a gum based thickener;
   at least one non-cationic germicide constituent selected from the group consisting of: parachlorometaxylenol, and halogenated carbanilides;
   at least 50% wt. of water; and,
   0.1-2% wt. of sodium borate as a pH adjusting agent and/or a pH buffer;
   wherein the composition exhibits a pH in the range of 7-10.5, and exhibits a viscosity of 1000-3000 cPs, when measured at 25° C.; and,
   wherein the composition exhibits a retention of initial color of the composition which is parity with a sample of the composition subsequent to 6 weeks storage at 40 deg.C.

3. A composition according to claim 1, wherein the composition further comprises 0.001-10% wt. of at least one organic solvent.

4. A composition according to claim 1, wherein the gum based thickener is xanthan gum, and excluded from the compositions are one or more different conventional thickeners based on naturally occurring or modified celluloses.

5. A composition according to claim 1 wherein the gum based thickener is xanthan gum, and which is the sole thickener present in the composition.

6. A composition according to claim 1 wherein the non-cationic germicide constituent is solely parachlorometaxylenol.

7. A composition according to claim 1 wherein the one or more inorganic abrasive particulate materials are inorganic carbonates.

8. A method of providing a cleaning and an antimicrobial benefit to a hard surface, which method comprises the step of:
   providing the aqueous, storage stable, abrasive containing hard surface treatment composition according to claim 1, to the said hard surface so to provide a cleaning and a sanitizing and/or antimicrobial benefit thereto.

9. A composition according to claim 1 wherein the halogenated carbanilides are selected from the group consisting of: 3,4,4'-trichlorocarbanilide, 3-trifluoromethyle-4,4-dichlorocarbanilide, and 3,3,4-trichlorocarbanilide.

10. A composition according to claim 2, wherein the composition further comprises 0.001-10% wt. of at least one organic solvent.

11. A composition according to claim 2, wherein the gum based thickener is xanthan gum, and excluded from the compositions are one or more different conventional thickeners based on naturally occurring or modified celluloses.

12. A composition according to claim 2, wherein gum based thickener is xantham gum, and which is the sole thickener present in the composition.

13. A composition according to claim 2, wherein the non-cationic germicide constituent is solely parachlorometaxylenol.

14. A composition according to claim 2, wherein the the one or more inorganic abrasive particulate materials are inorganic carbonates.

* * * * *